US010660838B2

(12) United States Patent
Hakozaki et al.

(10) Patent No.: US 10,660,838 B2
(45) **Date of Patent: *May 26, 2020**

(54) COMPOSITION AND METHOD FOR IMPROVING THE APPEARANCE OF SKIN

(71) Applicant: The Procter & Gamble Company, Cincinnati, OH (US)

(72) Inventors: Tomohiro Hakozaki, Cincinnati, OH (US); John Erich Oblong, Loveland, OH (US); Bin Fang Deyer, Loveland, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/015,502

(22) Filed: Jun. 22, 2018

(65) Prior Publication Data

US 2018/0369110 A1 Dec. 27, 2018

Related U.S. Application Data

(60) Provisional application No. 62/523,840, filed on Jun. 23, 2017.

(51) Int. Cl.

| | |
|---|---|
| ***A61K 8/60*** | (2006.01) |
| ***A61K 8/34*** | (2006.01) |
| ***A61K 8/67*** | (2006.01) |
| ***A61Q 19/00*** | (2006.01) |
| ***A61Q 19/08*** | (2006.01) |

(52) U.S. Cl.

CPC ................ *A61K 8/60* (2013.01); *A61K 8/342* (2013.01); *A61K 8/675* (2013.01); *A61Q 19/00* (2013.01); *A61Q 19/08* (2013.01); *A61K 2800/48* (2013.01)

(58) Field of Classification Search

CPC .......... A61K 8/60; A61K 8/342; A61K 8/675; A61K 2800/48; A61Q 19/00

USPC .......................................................... 514/23

See application file for complete search history.

(56) References Cited

U.S. PATENT DOCUMENTS

| | | | | |
|---|---|---|---|---|
| 3,859,436 | A | 1/1975 | Jacobi | |
| 6,638,519 | B1 | 10/2003 | Lorant | |
| 7,815,900 | B1 | 10/2010 | Cannell et al. | |
| 8,911,774 | B2 | 12/2014 | Giampapa | |
| 9,833,398 | B2 * | 12/2017 | Hakozaki | A61K 8/361 |
| 2002/0042438 | A1 | 4/2002 | Pelletier | |
| 2002/0193264 | A1 | 12/2002 | Cannell et al. | |
| 2007/0231288 | A1 | 10/2007 | Arnaud et al. | |
| 2008/0312169 | A1 | 12/2008 | Johnson et al. | |
| 2009/0197819 | A1 | 8/2009 | Johnson et al. | |
| 2009/0232750 | A1 | 9/2009 | St. Cyr | |
| 2010/0203175 | A1 * | 8/2010 | Abdul-Malak | A61K 8/347 424/734 |
| 2010/0291190 | A1 | 11/2010 | Giampapa | |
| 2011/0172160 | A1 | 7/2011 | Cao | |
| 2015/0209261 | A1 | 7/2015 | Ross | |

FOREIGN PATENT DOCUMENTS

| | | | |
|---|---|---|---|
| CN | 103565721 | A | 2/2014 |
| CN | 104274340 | A | 1/2015 |
| DE | 20220609 | U1 | 12/2003 |
| EP | 1417954 | A1 | 5/2004 |
| EP | 3040065 | A1 | 7/2016 |
| ES | 2542529 | T3 | 8/2015 |
| FR | 2938188 | A1 | 5/2010 |
| FR | 2975295 | A1 | 11/2012 |
| FR | 2986429 | A1 | 8/2013 |
| FR | 2989891 | A1 | 11/2013 |
| JP | 2009024075 | A | 2/2009 |
| JP | 2009269919 | A | 11/2009 |
| KR | 20050006622 | A | 1/2005 |
| WO | WO2007101493 | A1 | 9/2007 |
| WO | WO2011074143 | A1 | 6/2011 |
| WO | WO2016034519 | A1 | 3/2016 |
| WO | WO2016142551 | A1 | 9/2016 |
| WO | WO2016188691 | A1 | 12/2016 |
| WO | WO2017123512 | A1 | 7/2017 |

OTHER PUBLICATIONS

Khalifah et al. Kinetics of Nonenzymatic Glycation of Ribonuclease A Leading to Advanced Glycation End Products. Paradoxical Inhibition by Ribose Leads to Facile Isolation of Protein Intermediate for Rapid Post-Amadori Studies. Biochemistry, vol. 35, No. 15, 1996, p. 4645-4654. (Year: 1996).*

Trojahn et al. Characterizing Facial Skin Ageing in Humans: Disentangling Extrinsic from Intrinsic Biological Phenomena. BioMed Research International, vol. 2015, Article ID 318586, 9 pages. http://dx.doi.org/10.1155/2015/318586 (online: Jan. 14, 2015) (Year: 2015).*

Eisele et al., The partial compositional characteristics of apple juice from 175 apple varieties, Journal of Food Composition and Analysis, vol. 18, No. 2-3, Mar. 1, 2005, pp. 213-221.

International Search Report and Written Opinion of the International Searching Authority, PCT/US2018/038903, dated Aug. 31, 2018, 16 pages.

Sinthupoom et al., Nicotinic acid and derivatives as multifunctional pharmacophores for medical applications, European Food Research and Technology, vol. 240, No. 1, Oct. 29, 2014, pp. 1-17.

www.gnpd.com Record ID: 3708793, Anti-Wrinkle Face Cream, Neogen Agecure, Mar. 2016.

* cited by examiner

*Primary Examiner* — Yih-Horng Shiao

(74) *Attorney, Agent, or Firm* — John G. Powell

(57) ABSTRACT

Low pH cosmetic compositions and methods for improving the appearance of skin. The low pH cosmetic compositions herein include a saccharide and, optionally, one or more additional skin care actives to improve the appearance of skin. The lower pH reduces or even eliminates some of the skin health and appearance drawbacks associated with saccharide induced glycation.

7 Claims, 2 Drawing Sheets

COMPOSITION AND METHOD FOR IMPROVING THE APPEARANCE OF SKIN

FIELD

The present disclosure is directed generally to a cosmetic method of providing a skin health and/or appearance benefit and compositions therefor. More specifically, the present disclosure is directed to methods and compositions that utilize ribose at low pH to provide a skin benefit without causing glycation.

BACKGROUND

Skin is the first line of defense against environmental insults that would otherwise damage sensitive underlying tissue and organs. For example, skin maintains a relatively water-impermeable barrier between an organism and its environment to prevent dehydration. Additionally, skin plays a key role in a person's physical appearance. Generally, most people desire to have younger, healthy looking skin. And to some of these people, the tell-tale signs of skin aging such as thinning skin, wrinkles, and age spots are an undesirable reminder of the disappearance of youth. As a result, treating the signs of aging in skin has become a booming business in youth-conscious societies. Treatments range from cosmetic creams and moisturizers to various forms of cosmetic surgery.

Numerous agents, both natural and synthetic, are known for use in skin care compositions marketed to treat various skin conditions, especially those associated with aging. One example of a well-known skin care agent is ribose. Ribose is a pentose monosaccharide used in the cosmetics industry to provide a variety of skin health benefits. US 2007/0231288 discloses the use of D-ribose in a cosmetic composition to improve the metabolism of skin cells, and thereby improve the function and appearance of the skin. U.S. Pat. No. 6,638,519 describes the use of sugars such as ribose in cosmetic composition as surfactants and moisturizing agents. U.S. Pat. No. 8,911,774 discloses a topical composition for anti-aging skin treatment, which includes D-ribose as "an essential material for the DNA repairing process."

However, sugars such as ribose can also damage skin thru glycation. Glycation is generally recognized as a non-enzymatic process involving a monosaccharide (e.g., glucose or ribose) that reacts with an amino group of an amino acid via a series of reactions characterized by the formation of advance glycation end products ("AGEs"). AGEs can lead to crosslinking of the proteins in skin, especially collagen and elastin, which can manifest as reduced skin elasticity, fine lines and wrinkles, and sallow looking skin. Glycation is also known to increase regularly with age and exposure to ultraviolet radiation.

Accordingly, it would be desirable to provide a cosmetic skin care composition that includes ribose but does not contribute to glycation in skin.

SUMMARY

A topical skin care composition for cosmetically treating a skin condition and/or improving the appearance is described herein. The composition comprises about 0.01% to about 15% of a saccharide incorporated into a dermatologically acceptable carrier. The composition has a pH of less 5.0. The composition is formulated such that the saccharide in the composition does not increase glycation in the collagen matrix of human skin.

Also disclosed is a method of using the low pH compositions of the present invention. The method comprises identifying a target portion of skin where treatment is desired and topically applying the cosmetic composition of the present invention to the target portion of skin during a treatment period. The treatment period should of sufficient length for the composition to improve the condition and/or appearance of the target skin portion.

DETAILED DESCRIPTION

Figure 1:
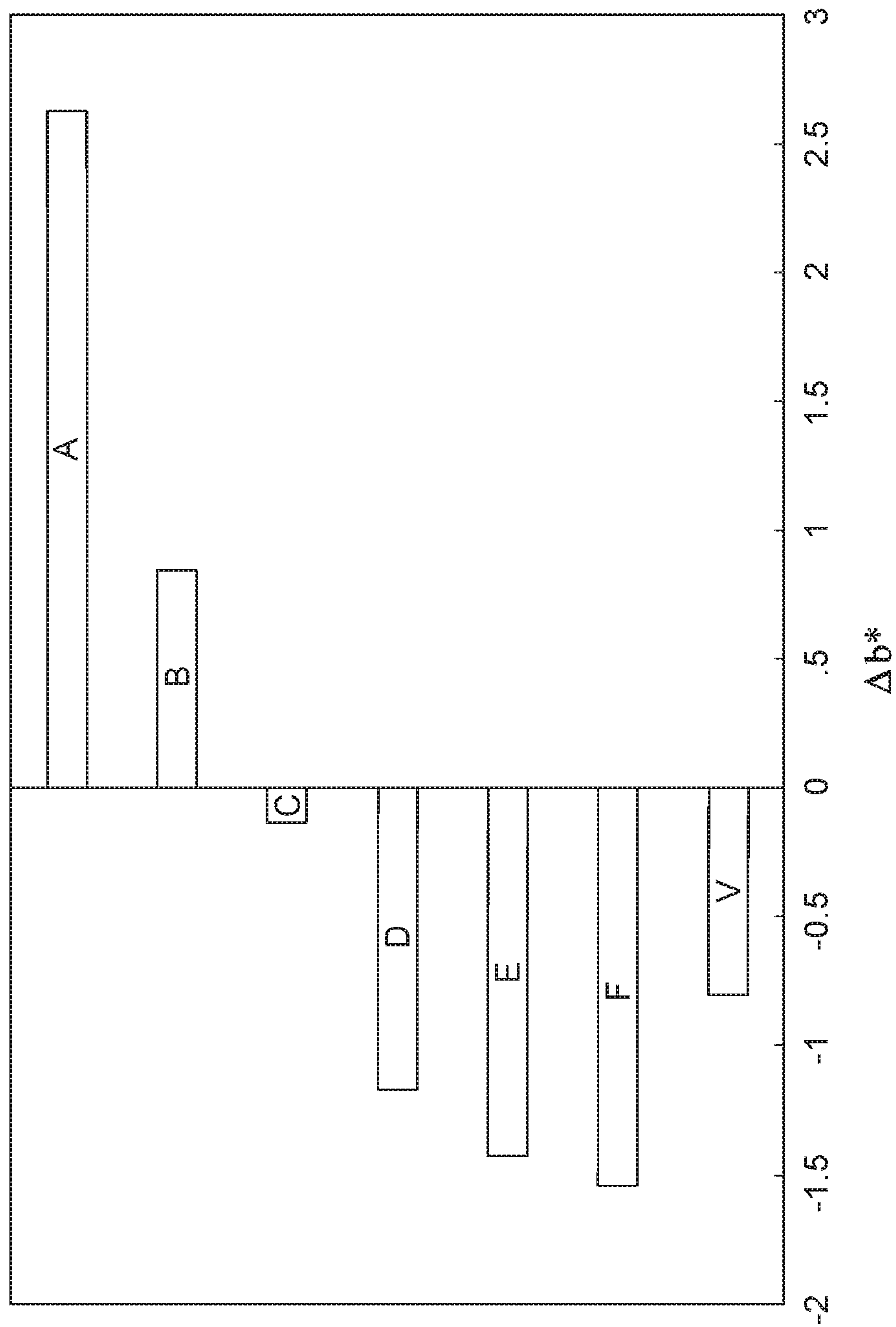
FIG. 1. is a chart illustrating the difference in yellowness for ribose-containing compositions at various pH.

The skin health benefits of saccharides such as ribose are well documented, but may not be suitable for use in some skin care compositions due to their prominent role in glycation. Surprisingly, it has now been discovered that when a saccharide such as ribose is included in a topical skin care composition at a relatively low pH, glycation associated with the saccharide(s) in the collagen matrix of skin can be significantly reduced.

Cosmetic compositions are commonly formulated to have a slightly acidic to slightly basic pH (e.g., pH 5.0 to 8.0) which is believed to improve the stability of certain ingredients in the composition (e.g., niacinamide, salicylates, and neutralized thickeners). However, formulating a skin care composition at a lower pH (e.g., less than pH 5.0, 4.5, 4.0, 3.5, 3.0, or even less than pH 2.5) appears to reduce glycation associated with sugars such as ribose in the collagen matrix of skin. In addition, an acidic skin composition may bolster the acid mantle of the skin, provide flexibility in other types of skin agents that can be included in the composition, and/or provide an exfoliation benefit.

Reference within the specification to "embodiment(s)" or the like means that a particular material, feature, structure and/or characteristic described in connection with the embodiment is included in at least one embodiment, optionally a number of embodiments, but it does not mean that all embodiments incorporate the material, feature, structure, and/or characteristic described. Furthermore, materials, features, structures and/or characteristics may be combined in any suitable manner across different embodiments, and materials, features, structures and/or characteristics may be omitted or substituted from what is described. Thus, embodiments and aspects described herein may comprise or be combinable with elements or components of other embodiments and/or aspects despite not being expressly exemplified in combination, unless otherwise stated or an incompatibility is stated.

In all embodiments, all percentages are by weight of the cosmetic composition, unless specifically stated otherwise. All ratios are weight ratios, unless specifically stated otherwise. All ranges are inclusive and combinable. The number of significant digits conveys neither a limitation on the indicated amounts nor on the accuracy of the measurements. All numerical amounts are understood to be modified by the word "about" unless otherwise specifically indicated. Unless otherwise indicated, all measurements are understood to be made at approximately 25° C. and at ambient conditions, where "ambient conditions" means conditions under about 1 atmosphere of pressure and at about 50% relative humidity. All numeric ranges are inclusive of narrower ranges; delineated upper and lower range limits are interchangeable to create further ranges not explicitly delineated.

The compositions of the present invention can comprise, consist essentially of, or consist of, the essential components as well as optional ingredients described herein. As used herein, "consisting essentially of" means that the composition or component may include additional ingredients, but only if the additional ingredients do not materially alter the basic and novel characteristics of the claimed compositions or methods. As used in the description and the appended claims, the singular forms "a," "an," and "the" are intended to include the plural forms as well, unless the context clearly indicates otherwise.

Definitions

"Apply" or "application", as used in reference to a composition, means to apply or spread the compositions of the present invention onto a human skin surface such as the epidermis.

"Cosmetic agent" means any substance, as well any component thereof, intended to be rubbed, poured, sprinkled, sprayed, introduced into, or otherwise applied to a mammalian body or any part thereof to provide a cosmetic effect. Cosmetic agents may include substances that are Generally Recognized as Safe (GRAS) by the US Food and Drug Administration, food additives, and materials used in non-cosmetic consumer products including over-the-counter medications.

"Effective amount" means an amount of a compound or composition sufficient to significantly induce a positive benefit to keratinous tissue over the course of a treatment period. The positive benefit may be a health, appearance, and/or feel benefit, including, independently or in combination, the benefits disclosed herein.

"Hyperpigmented" and "hyperpigmented spot" mean a localized portion of skin with relatively high melanin content. Examples of hyperpigmented spots include, but are not limited to age spots, melasma, chloasma, freckles, post-inflammatory hyperpigmentation, sun-induced pigmented blemishes, and the like.

"Improve the appearance of" means providing a measurable, desirable change or benefit in male and/or female skin appearance, which may be quantified, for example, by a reduction in the Spot Area Fraction of a hyperpigmented spot and/or a decrease in b* value of sallow skin. Exemplary methods for determining improvements in appearance are described in more detail below.

"L*a*b*" refers to the commonly recognized color space specified by the International Commission on Illumination ("CIE"). The three coordinates represent (i) the lightness of the color (i.e., L*=0 yields black and L*=100 indicates diffuse white), (ii) the position of the color between magenta and green (i.e., negative a* values indicate green while positive a* values indicate magenta) and (iii) the position of the color between yellow and blue (i.e., negative b* values indicate blue and positive b* values indicate yellow).

"Low pH," as used herein, refers to cosmetic compositions that have a pH of less than 4.0, but typically greater than 1.0. A suitable method of determining the pH of a composition is described in more detail below.

"Saccharide" means a sugar. Saccharides herein can be mono-, di-, oligo-, or polysaccharides; sugar acids; sugar derivatives; or modified sugars.

"Safe and effective amount" means an effective amount of an ingredient that is low enough to avoid serious side effects (within the scope of sound medical judgment).

"Sallow," when referring to the appearance of skin herein, means an unusual yellow or pale skin tone, with regard to a particular individual, which is commonly associated with an unhealthy state. Sallow-appearing skin can be diagnosed objectively (e.g., with a color value such as L* or b*) or subjectively (e.g., by a skin care professional or consumer).

"Skin care" means regulating and/or improving a skin condition. Some nonlimiting examples include improving skin appearance and/or feel by providing a smoother, more even appearance and/or feel; increasing the thickness of one or more layers of the skin; improving the elasticity or resiliency of the skin; improving the firmness of the skin; and reducing the oily, shiny, and/or dull appearance of skin, improving the hydration status or moisturization of the skin, improving the appearance of fine lines and/or wrinkles, improving skin exfoliation or desquamation, plumping the skin, improving skin barrier properties, improve skin tone, reducing the appearance of redness or skin blotches, and/or improving the brightness, radiancy, or translucency of skin.

"Skin care active" means a compound or combination of compounds that, when applied to skin, provide an acute and/or chronic benefit to skin or a type of cell commonly found therein. Skin care actives may regulate and/or improve skin or its associated cells (e.g., improve skin elasticity, hydration, skin barrier function, and/or cell metabolism).

"Skin care composition" means a composition that includes a skin care active and regulates and/or improves skin condition.

"Skin tone" means the overall appearance of basal skin color or color evenness. Skin tone is typically characterized over a larger area of the skin, which is generally more than 100 $mm^2$, up to and including the entirety of the facial skin or other bodily skin surface (e.g., arms, legs, back, hands, neck, chest and abdomen). Skin tone can be measured by image analysis. One measure of skin tone is lightness, which can be measured by the L* coordinate in the L*a*b* color space (International Commission on Illumination). Chromophore mapping such as melanin mapping and melanin concentration may also be used as an indicator of skin tone. Mean melanin may be calculated from the chromophore map data. Additionally, skin tone can be correlated to melanin evenness (e.g., standard deviation) which also may be calculated from the chromophore map data.

"Treatment period," as used herein, means the length of time and/or frequency that a material or composition is applied to a target skin surface.

"Vehicle control" means a negative control that is identical to the test composition except that it does include the particular active(s) of interest (e.g., does not contain ribose).

Cosmetic Compositions

The cosmetic compositions herein are intended for topical application to skin. The present compositions may be used to treat a variety of skin conditions such as, for example, those associated with or caused by inflammation; sun damage; aging (intrinsic or extrinsic); hyperpigmentation (e.g., age spots); seborrheic keratosis; actinic keratosis; UV exposure; skin sallowness or yellowness; skin dullness; skin redness; sebum secretion; rough texture, wrinkles, compromised skin barrier (e.g., dry skin); contact dermatitis; atopic dermatitis; eczema; keratinization disorders; psoriasis; wound healing; and the like.

These cosmetic compositions herein include an effective amount of a suitable saccharide such as ribose (e.g., D-ribose) and a dermatologically acceptable carrier. The present composition may optionally include one or more skin actives of the type commonly included in cosmetic skin care compositions. Non-limiting examples of saccharides that may be suitable for use herein include trioses such as glyceraldehyde and dihydroxyacetone; tetroses such as erythrose, threose, erythrulose; pentoses such as ribose, arabinose, ribulose, xylulose, xylose, lyxose, deoxyribose, dibulose, ribonic acid, and ribaric acid; hexoses such as allose, altrose, glucose, galactose, mannose, fructose, idose, talose, psicose, sorbose, tagatose, gulose, fucose, rhamnose, glucuronic acid, aldose, aldonic acid, glucaric acid, gularic acid, galactaric acid, galacturonic acid; heptoses such as sedoheptulose; nonoses such as neuraminic acid; saccharide derivatives such as ribulose 5-phosphate, xylulose 5-phosphate, ribose 5-phosphate, sedoheptulose 7-phosphate, glyceraldehyde 3-phosphate, fructose 6-phosphate, erythrose 4-phosphate, glucose 6-phosphate, 6-phosphoglucono-δ-lactone, 6-phosphogluconate, dihydroxyacetone phosphate, fructose 1,6-bisphosphate; glycosides such as xyloside; xylitol; trehalose; and modified saccharides such as N-acetylglucosamine, N-acetylgalactosamine, and glucosamine A particularly suitable saccharide for use herein is RIBOXYL brand ribose available from Lucas Meyer Cosmetics, France. The saccharide may be present at between 0.05% and 15% by weight of the composition (e.g., 1%, to 15%, 2% to 10%, 3% to 8% or even 4% to 6%).

The cosmetic compositions herein are formulated to have a relatively low pH (e.g., less than 5.0, 4.5, 4.0, 3.5, 3.0, or even less than 2.5) and may be provided in various product forms that include, but are not limited to, solutions, suspensions, lotions, creams, gels, toners, sticks, sprays, aerosols, ointments, cleansing liquid washes and solid bars, pastes, foams, mousses, shaving creams, wipes, strips, patches, electrically-powered patches, hydrogels, film-forming products, facial and skin masks (with and without insoluble sheet), make-up such as foundations, eye liners, and eye shadows, and the like. The cosmetic composition form may follow from the particular dermatologically acceptable carrier chosen, if present in the composition. The cosmetic compositions herein may be made using conventional methods of making such compositions.

Dermatologically Acceptable Carrier

The compositions herein include a dermatologically acceptable carrier (which may be referred to as a "carrier"). The phrase "dermatologically acceptable carrier" means that the carrier is suitable for topical application to the keratinous tissue, has good aesthetic properties, is compatible with the actives in the composition, and will not cause any unreasonable safety or toxicity concerns. In one embodiment, the carrier is present at a level of from about 50% to about 99%, about 60% to about 98%, about 70% to about 98%, or, alternatively, from about 80% to about 95%, by weight of the composition.

The carrier can be in a wide variety of forms. In some instances, the solubility or dispersibility of the components (e.g., extracts, sunscreen active, additional components) may dictate the form and character of the carrier. Non-limiting examples include simple solutions (e.g., aqueous or anhydrous), dispersions, emulsions, and solid forms (e.g., gels, sticks, flowable solids, or amorphous materials). In certain embodiments, the dermatologically acceptable carrier is in the form of an emulsion. Emulsion may be generally classified as having a continuous aqueous phase (e.g., oil-in-water and water-in-oil-in-water) or a continuous oil phase (e.g., water-in-oil or oil-in-water). The oil phase of the present invention may comprise silicone oils, non-silicone oils such as hydrocarbon oils, esters, ethers, and mixtures thereof. The aqueous phase typically comprises water and water-soluble ingredients (e.g., water-soluble moisturizing agents, conditioning agents, anti-microbials, humectants and/or other skin care actives). However, in some instances, the aqueous phase may comprise components other than water, including but not limited to water-soluble moisturizing agents, conditioning agents, anti-microbials, humectants and/or other water-soluble skin care actives. In some instances, the non-water component of the composition comprises a humectant such as glycerin and/or other polyol(s). Emulsions may also contain an emulsifier, e.g., from about 1% to about 10% or from about 2% to about 5% based on the weight of the carrier. Emulsifiers may be nonionic, anionic or cationic. Some suitable emulsifiers are disclosed in, for example, U.S. Pat. No. 3,755,560, issued Aug. 28, 1973, Dickert et al; U.S. Pat. No. 4,421,769, issued Dec. 20, 1983, Dixon et al.; and McCutcheon's Detergents and Emulsifiers, North American Edition, pages 317-324 (1986), each incorporated herein by reference.

The carrier may contain one or more dermatologically acceptable, hydrophilic diluents. As used herein, "diluent" includes materials in which the niacinamide and/or saccharide can be dispersed, dissolved, or otherwise incorporated. Hydrophilic diluents include water, organic hydrophilic diluents such as lower monovalent alcohols (e.g., C1-C4) and low molecular weight glycols and polyols, including propylene glycol, polyethylene glycol (e.g., Molecular Weight 200-600 g/mole), polypropylene glycol (e.g., Molecular Weight 425-2025 g/mole), glycerol, butylene glycol, 1,2,4-butanetriol, sorbitol esters, 1,2,6-hexanetriol, ethanol, isopropanol, sorbitol esters, butanediol, ether propanol, ethoxylated ethers, propoxylated ethers and combinations thereof.

Thickeners

In some instances, it may be desirable to use thickeners that tolerate a lower range of pH ("stable fatty alcohol thickener"). For example, neutralized thickeners may degrade at lower pH and thus may not impart the desired thickening or feel properties to the composition. On the other hand, fatty alcohol thickeners such as cetyl alcohols and stearyl alcohols are generally stable at low pH (e.g., pH of less than 5.0 or even between a pH of about 2.5 to about 4.0), and thus particularly suited for use in the low pH compositions herein. Accordingly, the present compositions may be free or substantially free of neutralized thickeners and/or may have from 0.1% to 10% (e.g., from about 0.5% to about 8%, from about 1.0% to about 5%, or even from about 2% to about 4%) of a stable fatty alcohol thickener.

Sunscreen Actives

In some instances, it may be desirable to include one or more sunscreen actives in the present composition. The compositions of the subject invention may comprise one or more sunscreen actives (or sunscreen agents) and/or ultraviolet light absorbers. Herein, "sunscreen active" includes both sunscreen agents and physical sunblocks. Sunscreen actives and ultraviolet light absorbers may be organic or inorganic. Examples of suitable sunscreen actives and ultraviolet light absorbers are disclosed in Personal Care Product. Council's International Cosmetic Ingredient Dictionary and Handbook, Thirteenth Edition, as "sunscreen agents." Particularly suitable sunscreen actives are 2-ethythexyl-p-methoxycinnamate (commercially available as PARSOL™ MCX), 4,4'-t-butyl methoxydibenzoyl-methane (commercially available as PARSOL™ 1789), 2-hydroxy-4-methoxybenzophenone, octyldimethyl-p-aminobenzoic acid, digalloyltrioleate, 2,2-dihydroxy-4-methoxybenzophenone, ethyl-4-(bis(hydroxypropyl))aminobenzoate, 2-ethylhexyl-2-cyano-3,3-diphenylacrylate, 2-ethylhexyl-salicylate, glyceryl-p-aminobenzoate, 3,3,5-trimethylcyclohexylsalicylate, menthyl anthranilate, p-dimethyl-aminobenzoic acid or aminobenzoate, 2-ethylhexyl-p-dimethyl-amino-benzoate, 2-phenylbenzimidazole-5-sulfonic acid, 2-(p-dimethylaminophenyl)-5-sulfonicbenzoxazoic acid, octocrylene, zinc oxide, benzylidene camphor and derivatives thereof, titanium dioxide, and mixtures thereof. The composition may include from about 1% to about 20% or even from about 2% to about 10% by weight of the composition, of the sunscreen active and/or ultraviolet light absorber. Exact amounts will vary depending upon the chosen sunscreen active and/or ultraviolet light absorber and the desired Sun Protection Factor (SPF), and are within the knowledge and judgment of one of skill in the art.

Other Optional Ingredients.

The present composition may optionally include one or more additional ingredients commonly used in cosmetic compositions (e.g., colorants, skin care actives, anti-inflammatory agents, sunscreen agents, emulsifiers, buffers, rheology modifiers, combinations of these and the like), provided that the additional ingredients do not undesirably alter the skin health or appearance benefits provided by the present compositions. The additional ingredients, when incorporated into the composition, should be suitable for use in contact with human skin tissue without undue toxicity, incompatibility, instability, allergic response, and the like. Some nonlimiting examples of additional actives include vitamins, minerals, peptides and peptide derivatives, sugar amines, sunscreens, oil control agents, particulates, flavonoid compounds, hair growth regulators, anti-oxidants and/or anti-oxidant precursors, preservatives, protease inhibitors, tyrosinase inhibitors, anti-inflammatory agents, moisturizing agents, exfoliating agents, skin lightening agents, sunless tanning agents, lubricants, anti-acne actives, anti-cellulite actives, chelating agents, anti-wrinkle actives, anti-atrophy actives, phytosterols and/or plant hormones, N-acyl amino acid compounds, antimicrobials, and antifungals. Other non-limiting examples of additional ingredients and/or skin care actives that may be suitable for use herein are described in U.S. Publication Nos. 2002/0022040; 2003/0049212; 2004/0175347; 2006/0275237; 2007/0196344; 2008/0181956; 2008/0206373; 2010/00092408; 2008/0206373; 2010/0239510; 2010/0189669; 2010/0272667; 2011/0262025; 2011/0097286; 2012/0197016; 2012/0128683; 2012/0148515; 2012/0156146; and 2013/0022557; and U.S. Pat. Nos. 5,939,082; 5,872,112; 6,492,326; 6,696,049; 6,524,598; 5,972,359; and 6,174,533.

When including optional ingredients in the compositions herein, it may be desirable to select ingredients that do not form complexes or otherwise undesirably interact with other ingredients in the composition at low pH, especially pH sensitive ingredients like niacinamide, salicylates and peptides. In some instances, it may be desirable to select skin care actives that function via different biological pathways so that the actives do not interfere with one another, which could reduce the efficacy of both agents. When present, the optional ingredients may be included at amounts of from 0.0001% to 50%; from 0.001% to 20%; or even from 0.01% to 10% (e.g., 50%, 40%, 30%, 20%, 10%, 5%, 4%, 3%, 2%, 1%, 0.5% or 0.1%), by weight of the composition.

Methods of Use

The present method includes identifying a target portion of skin (e.g., a facial skin surface such as the forehead, perioral, chin, periorbital, nose, and/or cheek) in need of treatment and applying a low pH composition comprising a saccharide (e.g., ribose), and optionally one or more additional skin care agents, to the target portion of skin. In some instances, the target portion of skin may have a sallow skin tone or exhibit some other undesirable skin condition. In some instances, the target portion of skin may not appear to be suffering from a skin condition such as one associated with the effects of glycation, but a user (e.g., a relatively young user) may still wish to target such an area of skin if it is one that typically exhibits the undesirable effects of glycation or some other skin condition later in life (e.g., skin surfaces that are typically not covered by clothing, such as facial skin surfaces, hand and arm skin surfaces, foot and leg skin surfaces, and neck and chest skin surfaces). In this way, the present compositions may be used in a preventative capacity. The composition may be applied to the target skin portion and, if desired, to the surrounding skin at least once a day, twice a day, or on a more frequent daily basis, during a treatment period. When applied twice daily, the first and second applications are separated by at least 1 to 12 hours. Typically, the composition is applied in the morning and/or in the evening before bed. When used according to the methods herein, the present composition may improve the appearance of a skin condition without causing glycation.

The treatment period is ideally of sufficient time for a skin active present in the low pH composition to improve the appearance of a target portion of skin. In some instances, the saccharide-containing, low pH compositions herein may even reduce glycation, for example, when compared to a vehicle control. The treatment period may last for at least 1 week (e.g., about 2 weeks, 4 weeks, 8 weeks, or even 12 weeks). In some instances, the treatment period will extend over multiple months (i.e., 3-12 months) or multiple years. In some instances, the composition may be applied most days of the week (e.g., at least 4, 5 or 6 days a week), at least once a day or even twice a day during a treatment period of at least 2 weeks, 4 weeks, 8 weeks, or 12 weeks.

The step of applying the composition may be accomplished by localized application. In reference to application of the composition, the terms "localized", "local", or "locally" mean that the composition is delivered to the targeted area (e.g., a hyperpigmented spot or portion thereof) while minimizing delivery to skin surfaces where treatment is not desired. The composition may be applied and lightly massaged into an area of skin. The form of the composition or the dermatologically acceptable carrier should be selected to facilitate localized application. While certain embodiments herein contemplate applying a composition locally to an area, it will be appreciated that compositions herein can be applied more generally or broadly to one or more skin surfaces. In certain embodiments, the compositions herein may be used as part of a multi-step beauty regimen, wherein the present composition may be applied before and/or after one or more other compositions.

Advanced Glycation End Product Assay

The AGE assay provides an in vitro method of determining how a test agent impacts glycation. In particular, a saccharide can be applied to gelatin, which acts as a surrogate for collagen (i.e., a heterogeneous mixture of high-average-molecular-mass, water-soluble proteins present in collagen), at a particular pH and the resulting AGEs detected by a spectrophotometer. When a saccharide such as ribose is added to the sample, it reacts with the proteins in the gelatin, much in the same way as it would with collagen, to produce AGEs. The spectrophotometer detects the fluorescence intensity ("FLR") or yellowness (b*) associated with the resulting AGEs, which can then be correlated to the amount of glycation that occurs in skin. Lower b* and FLR values correspond to less AGEs, and thus less glycation.

Three replicates of each test samples are prepared in a 96-well plate (e.g., a FALCON brand 96-well tissue culture plate or equivalent) at a total volume of 250 μl/well. The plate(s) containing the test samples are placed in a standard cell culture incubator (e.g., THERMO SCIENTIFIC FORMA brand incubator available from Fisher Scientific, Waltham, MA or equivalent) and incubated for the duration of the test at 37° C. with 5% $CO_2$ and 95% relative humidity. Fluorescence intensity and yellowness are measured at the start of test (time=0) and generally monitored on a daily basis except for weekends. To measure FLR or b*, the plate(s) containing the test samples are removed from the incubator and placed in a SPECTRAMAX Plus brand spectrophotometer (available from Molecular Devices, Sunnyvale, California) or equivalent. To detect fluorescence intensity ("FLR"), the spectrophotometer is set at 400/465 nm (ex/em). To detect yellowness (b*), the spectrophotometer is set to collect absorbance spectrum from 350 nm to 750 nm in 10 nm increments. The absorbance spectra from the yellowness measurement are then converted to L*a*b* values by a computer using suitable conversion software.

The change in fluorescence intensity ("ΔFLR") is determined by comparing the FLR of a well at a sampling time point to the initial FLR at time=0. The change in yellowness ("Δb*") at a particular time point is determined by comparing the initial b* value at time=0 to the b* value at the time point of interest.

EXAMPLE

The effect of pH on glycation was determined for a ribose-containing composition across a range of pH (i.e., pH 6.8, 5, 4.5, 4, 3.5, and 2.5). The test samples were prepared in triplicate of 1-ml volume for each testing leg to accommodate threshold volume needed for small volume pH titration process. Each 1-ml volume of sample is made using a combination of 450 ul of 2% w/v gelatin solution (available from Sigma as Catalog # G1393), 100 ul of 25.9% w/v ribose solution (available from Sigma, Catalog # R7500-25G), and a sufficient quantity of Dulbecco's phosphate buffered saline ("DPBS") (available from Gibco's) to bring the sample volume to 1 ml. 1N HCl was used to adjust the pH of the sample to the desired level. After the 1-ml batches are made in triplicate for each treatment leg, 250 ul from each batch is delivered to each well onto a 96-well plate. Each well should contain 112.5 ul of 2% gelatin, 10 ul of 25.9% w/v Ribose solution, and 127.5 ul of DPBS/1N HCl, for a ribose concentration of 2.59% w/v. The vehicle control contained 112.5 μl gelatin and 137.5 μl DPBS and had an unadjusted pH of 6.7.

Figure 2:
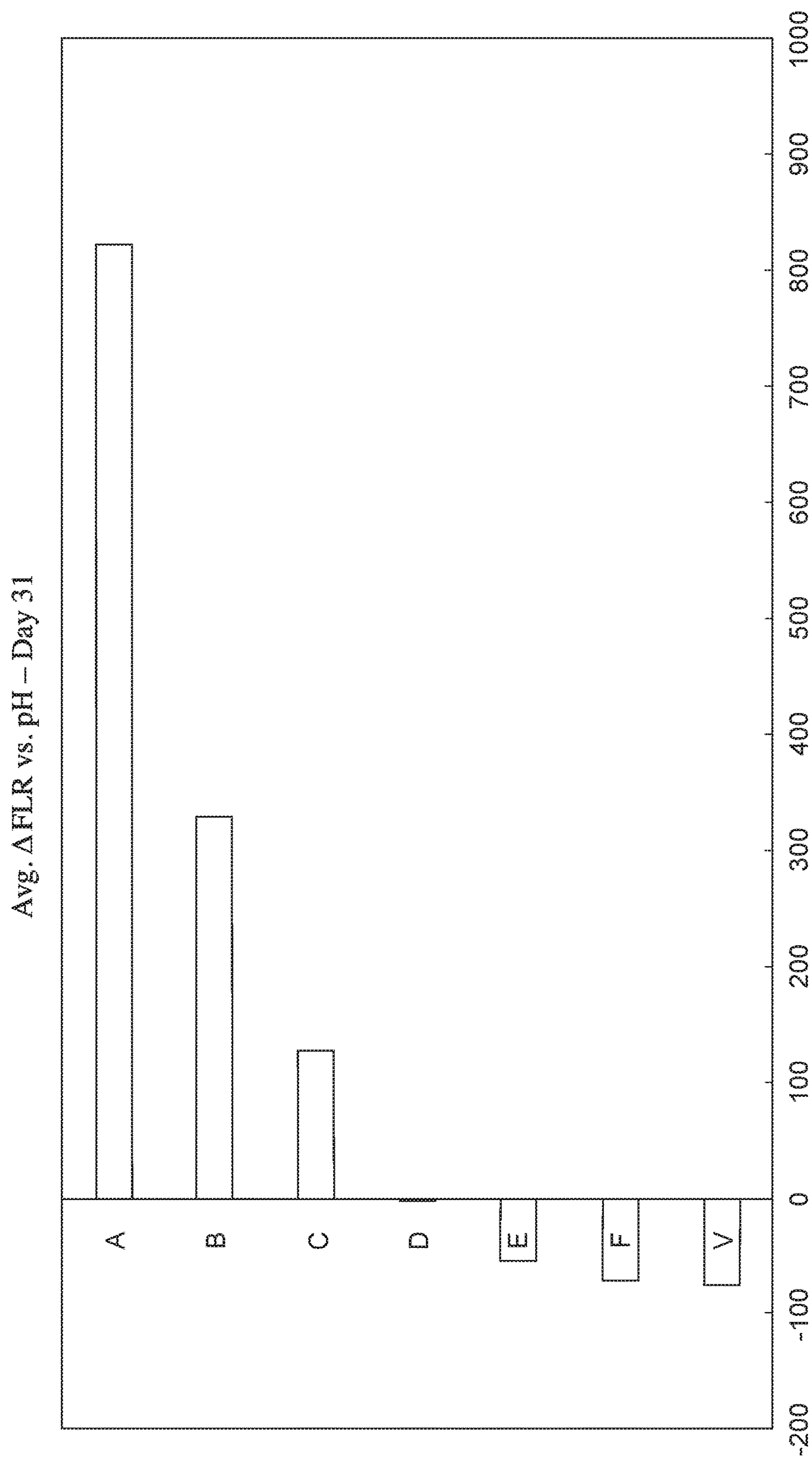
FIG. 2 is a chart illustrating the difference in FLR for ribose-containing compositions at various pH.

The average ΔFLR and Δb* in this example were determined for each test sample according to the AGE Assay described above. The duration of the test was 38 days. The pH for each test sample is shown in Table 1. Composition A was used as a positive control and Composition V is the vehicle control. The results of the test are summarized in Tables 2 to 7 below. The results at day 31 are illustrated in FIGS. 1 and 2.

TABLE 1

| Composition | pH |
|---|---|
| A (pos. control) | 6.8 |
| B | 5 |
| C | 4.5 |
| D | 4.0 |
| E | 3.5 |
| F | 2.5 |
| V (neg. control) | 6.7 |

TABLE 2

| Composition | ΔFLR at 20 days | p-value vs. A | p-value vs. V |
|---|---|---|---|
| A | 462 | 1.000 | 0.000 |
| B | 103 | 0.000 | 0.000 |
| C | −3 | 0.000 | 0.000 |
| D | −56 | 0.000 | 0.231 |
| E | −63 | 0.000 | 0.954 |
| F | −68 | 0.000 | 0.297 |
| V | −62 | 0.000 | 1.000 |

TABLE 3

| Composition | Δb* at 20 days | p-value vs. A | p-value vs. V |
|---|---|---|---|
| A | 0.868 | 1.000 | 0.000 |
| B | −0.334 | 0.000 | 0.017 |
| C | −1.026 | 0.000 | 0.386 |
| D | −1.510 | 0.000 | 0.010 |
| E | −1.502 | 0.000 | 0.011 |
| F | −1.409 | 0.000 | 0.019 |
| V | −0.897 | 0.000 | 1.000 |

TABLE 4

| Composition | ΔFLR at 31 days | p-value vs. A | p-value vs. V |
|---|---|---|---|
| A | 822 | 1.000 | 0.000 |
| B | 329 | 0.000 | 0.000 |
| C | 127 | 0.000 | 0.000 |
| D | −2 | 0.000 | 0.000 |
| E | −55 | 0.000 | 0.022 |
| F | −71 | 0.000 | 0.426 |
| V | −75 | 0.000 | 1.000 |

TABLE 5

| Composition | Δb* at 31 days | p-value vs. A | p-value vs. V |
|---|---|---|---|
| A | 2.625 | 1.000 | 0.000 |
| B | 0.845 | 0.000 | 0.001 |
| C | −0.135 | 0.000 | 0.017 |
| D | −1.173 | 0.000 | 0.084 |
| E | −1.426 | 0.000 | 0.016 |
| F | −1.540 | 0.000 | 0.007 |
| V | −0.799 | 0.000 | 1.000 |

TABLE 6

| Composition | ΔFLR at 38 days | p-value vs. A | p-value vs. V |
|---|---|---|---|
| A | 964 | 1.000 | 0.000 |
| B | 463 | 0.000 | 0.000 |
| C | 214 | 0.000 | 0.000 |
| D | 39 | 0.000 | 0.000 |
| E | −50 | 0.000 | 0.004 |

TABLE 6-continued

| Composition | ΔFLR at 38 days | p-value vs. A | p-value vs. V |
|---|---|---|---|
| F | −79 | 0.000 | 0.103 |
| V | −91 | 0.000 | 1.000 |

TABLE 7

| Composition | Δb* at 38 days | p-value vs. A | p-value vs. V |
|---|---|---|---|
| A | 3.771 | 1.000 | 0.000 |
| B | 1.728 | 0.000 | 0.000 |
| C | 0.504 | 0.000 | 0.000 |
| D | −0.811 | 0.000 | 0.239 |
| E | −1.338 | 0.000 | 0.126 |
| F | −1.560 | 0.000 | 0.015 |
| V | −1.033 | 0.000 | 1.000 |

Composition A, which acted as the positive control, showed a continual increase in FLR and yellowness over time as expected. Composition B showed an increase FLR at day 20, 31, and 38, but only showed an increase in yellowness at days 31 and 38. But even at day 20, the decrease in yellowness for composition B significantly improved relative to the negative control (i.e., composition V). Compositions C, D, E, and F exhibited a trend of decreasing fluorescence and yellowness corresponding to the decrease in pH. Surprisingly, compositions D, E, and F even showed an improvement (i.e., decrease) in b* relative to the vehicle control, which suggests that saccharides such as ribose may actually be useful in combatting certain aspects of glycation at lower pH. Thus, it is important to formulate skin care composition that include saccharides such as ribose at lower pH to avoid or even combat the undesirable effects of glycation. Accordingly, the present compositions may reduce the presence of AGEs and/or yellowness in skin when used according to the methods described.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method of treating a skin condition of a user without increasing glycation in the collagen of the user, comprising:

(a) identifying a target portion of skin where treatment is desired; and (b) topically applying a cosmetic composition to the target portion of skin during a treatment period, wherein the composition comprises (i) about 0.01% to about 15% by weight of a saccharide, (ii) a dermatologically acceptable carrier, wherein the composition has a pH of less than 5.0, and wherein the treatment period is sufficient for the composition to improve the skin condition and the composition does not increase glycation relative to a vehicle control in the Advanced Glycation End Product (AGE) Assay.

2. The method of claim 1, wherein the composition does not increase a b* value in the AGE assay.

3. The method of claim 1, wherein the composition does not increase a fluorescence intensity value in the AGE Assay.

4. The method of claim 1, wherein the pH is between about 2.5 and 4.0.

5. The method of claim 1, wherein the saccharide is ribose.

6. The method of claim 1, further comprising from about 0.1% to about 10% by weight of a stable fatty alcohol thickener.

7. The method of claim 1, wherein the composition reduces glycation relative to a vehicle control in the Advanced Glycation End Product (AGE) Assay.

* * * * *